(12) United States Patent
Lin

(10) Patent No.: US 10,531,686 B2
(45) Date of Patent: Jan. 14, 2020

(54) ANTI-LEAKAGE LIQUID STORAGE DEVICE OF ELECTRONIC CIGARETTE

(71) Applicant: SHENZHEN HAPPY VAPING TECHNOLOGY LIMITED, Shenzhen, Guangdong (CN)

(72) Inventor: Guangrong Lin, Guangdong (CN)

(73) Assignee: SHENZHEN HAPPY VAPING TECHNOLOGY LIMITED, Shenzhen (CN)

( * ) Notice: Subject to any disclaimer, the term of this patent is extended or adjusted under 35 U.S.C. 154(b) by 457 days.

(21) Appl. No.: 15/315,391

(22) PCT Filed: Dec. 1, 2014

(86) PCT No.: PCT/CN2014/092635
§ 371 (c)(1),
(2) Date: Dec. 1, 2016

(87) PCT Pub. No.: WO2015/184751
PCT Pub. Date: Dec. 10, 2015

(65) Prior Publication Data
US 2017/0188631 A1 Jul. 6, 2017

(30) Foreign Application Priority Data

Jun. 5, 2014 (CN) ..................... 2014 2 0295789 U

(51) Int. Cl.
*A24F 47/00* (2006.01)
*A61M 15/06* (2006.01)

(52) U.S. Cl.
CPC ............ *A24F 47/008* (2013.01); *A24F 47/00* (2013.01); *A61M 15/06* (2013.01)

(58) Field of Classification Search
CPC .............................. A24F 47/008; A61M 15/06
See application file for complete search history.

(56) References Cited

U.S. PATENT DOCUMENTS 4,932,941 A * 6/1990 Min ................... A61M 5/5013
604/110
2014/0069425 A1 * 3/2014 Zhang ................. A24F 47/008
128/202.21

(Continued)

FOREIGN PATENT DOCUMENTS

| CN | 103584287 A | 2/2014 |
| CN | 203563693 U | 4/2014 |

OTHER PUBLICATIONS

International Search Report of PCT Patent Application No. PCT/CN2014/092635 dated Mar. 4, 2015.

*Primary Examiner* — Anthony Calandra

(57) ABSTRACT

Disclosed is an anti-leakage liquid storage device for electronic cigarette, including a cylindrical liquid storage cup, at least two locking members arranged at an inner wall of a liquid outlet end of the liquid storage cup, a liquid percolation piece having a plurality of liquid percolation holes and having a circular edge which engages with an internal circumferential surface of the liquid outlet end of the liquid storage cup, and a filter piece with one side thereof abutting against the liquid percolation piece; wherein the other side of the filter piece abuts against an annular pressing plate, the annular pressing plate has a circular edge which engages with the internal circumferential surface of the liquid outlet end; the annular pressing plate is locked by the at least two locking members and tightly presses the filter piece and the liquid percolation piece.

1 Claim, 4 Drawing Sheets

(56) References Cited

U.S. PATENT DOCUMENTS

2014/0150783 A1\* 6/2014 Liu .................. A24F 47/008
                                              128/202.21
2017/0006916 A1\* 1/2017 Liu .................. A24F 47/008
2017/0117654 A1\* 4/2017 Cruz ................ H01R 13/2421

\* cited by examiner

ANTI-LEAKAGE LIQUID STORAGE DEVICE OF ELECTRONIC CIGARETTE

FIELD OF THE INVENTION

The present invention relates to an electronic cigarette, especially relates to an anti-leakage liquid storage device of an electronic cigarette.

BACKGROUND OF THE INVENTION

Chinese patent application No. 201320785583.4 discloses a liquid storage device of a cotton-free electronic cigarette, the liquid storage device has a simple structure, a strong connection and an easy assembly method over prior arts. The liquid storage device of the cotton-free electronic cigarette comprises a liquid storage cup for storing cigarette liquid, and a liquid percolation piece having a plurality of liquid percolation holes; wherein the liquid storage cup has a cylindrical shape, an inner wall of a liquid outlet end of the liquid storage cup is provided with at least two locking members, the liquid percolation piece has a circular edge which engages with an internal circumferential surface of the liquid outlet end of the liquid storage cup, the liquid percolation piece is inserted into the liquid outlet end of the liquid storage cup and is passed through the at least two locking members to be locked. Preferably, a filter piece is placed between the liquid percolation piece and the locking members and abuts against the liquid percolation piece; a heating element of a vaporization assembly is close to the liquid percolation piece and the filter piece. However, when cigarette liquid filled in the liquid storage device passes the liquid percolation piece to be absorbed by the filter piece, the filter piece filled with the cigarette liquid will easily become soft and deformed, as a result the deformed filter piece would fall off and separate from the liquid percolation piece which leads to the leakage of the cigarette liquid. The leaked cigarette liquid that has not been fully vaporized would be inhaled into a user's mouth, which greatly decreases the user's experience.

SUMMARY OF THE INVENTION

In order to solve the cigarette liquid leakage problem of existing cotton-free electronic cigarettes, the present invention aims to provide an anti-leakage liquid storage device for electronic cigarettes.

The technical solution of the present invention is an anti-leakage liquid storage device of an electronic cigarette, comprising a cylindrical liquid storage cup, at least two locking members arranged at an inner wall of a liquid outlet end of the liquid storage cup, a liquid percolation piece having a plurality of liquid percolation holes and having a circular edge which engages with an internal circumferential surface of the liquid outlet end of the liquid storage cup, and a filter piece with one side thereof abutting against the liquid percolation piece; wherein the other side of the filter piece abuts against an annular pressing plate, the annular pressing plate has a circular edge which engages with the internal circumferential surface of the liquid outlet end of the liquid storage cup; the annular pressing plate is locked by the at least two locking members and tightly presses the filter piece and the liquid percolation piece.

Preferably, the annular pressing plate is formed integrally with at least one reinforcing rib at the middle thereof.

The technical solutions of the present invention have the following advantages. The other side of the filter piece is arranged with the annular pressing plate. The annular pressing plate tightly presses the filter piece and the liquid percolation piece after it has been locked by the at least two locking members. When the cigarette liquid filled in the liquid storage device passes the liquid percolation piece to be absorbed by the filter piece, due to the fixation effect of the annular pressing plate, the filter piece filled with the cigarette liquid will not become deformed or separate from the liquid percolation piece after the filter piece has become soft. Because the leakage of the cigarette liquid is prevented, the cigarette liquid will not be inhaled into a user's mouth, which greatly increases user's experience and the use efficiency of the electronic cigarette.

DETAILED DESCRIPTION OF ILLUSTRATED EMBODIMENTS

Various preferred embodiments will now be described with reference to the figures.

Figure 1:
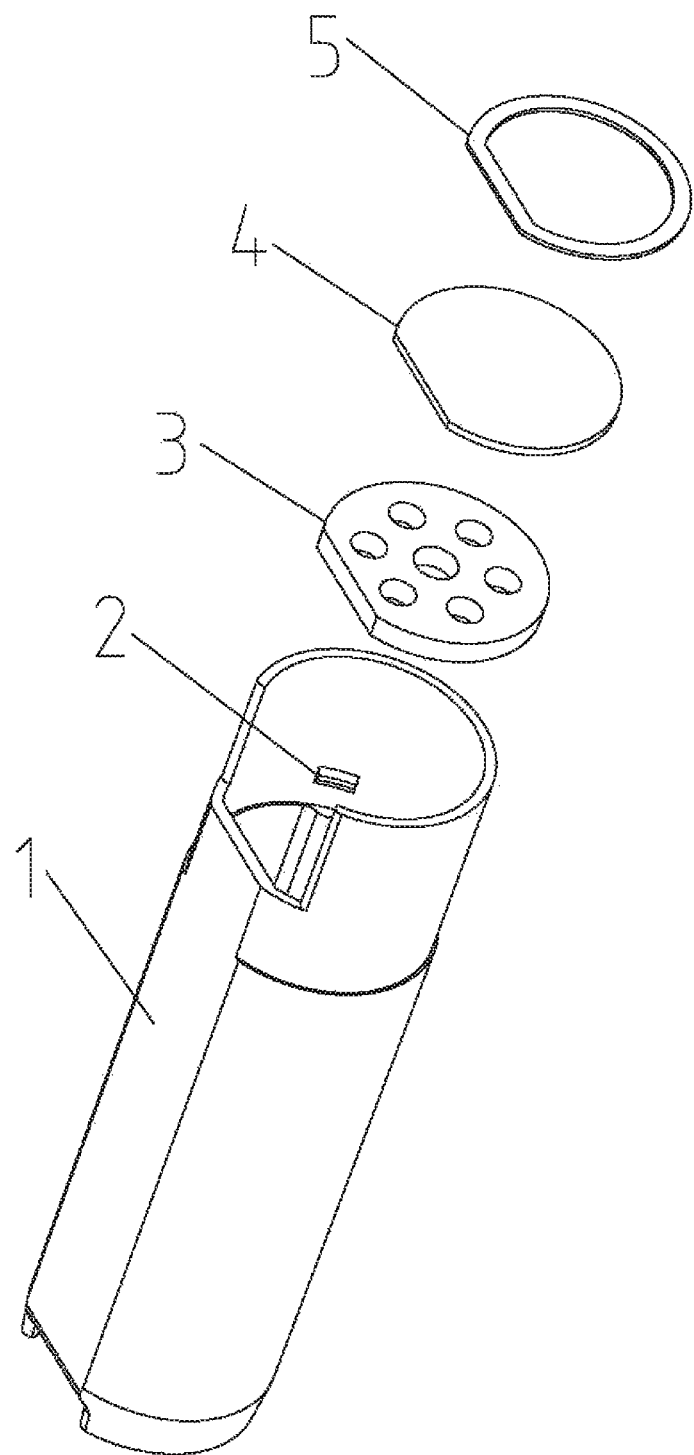
FIG. 1 is a perspective exploded view showing a first embodiment of an anti-leakage liquid storage device of an electronic cigarette of the present invention.
Figure 2:
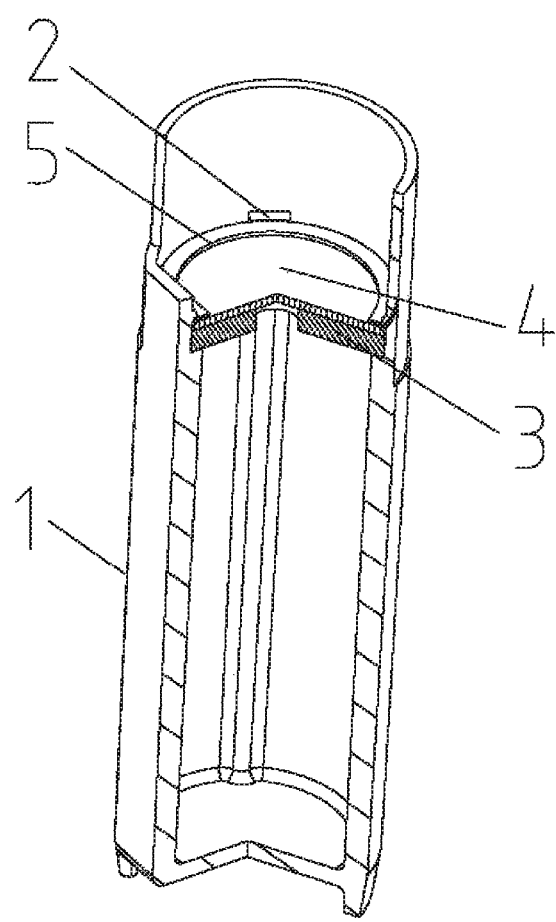
FIG. 2 is a schematic view of an assembled anti-leakage liquid storage device shown in FIG. 1, the anti-leakage liquid storage device being partially sectioned.

FIG. 1 and FIG. 2 show a first embodiment of an anti-leakage liquid storage device of an electronic cigarette of the present invention.

Referring to FIG. 1 and FIG. 2, an anti-leakage liquid storage device of an electronic cigarette comprises a cylindrical liquid storage cup 1, at least two locking members 2 arranged at an inner wall of a liquid outlet end of the liquid storage cup 1, a liquid percolation piece 3 having a plurality of liquid percolation holes and having a circular edge which engages with an internal circumferential surface of the liquid outlet end of the liquid storage cup 1, a filter piece 4 with one side thereof abutting against the liquid percolation piece 3, and an annular pressing plate 5 abutting against the other side of the filter piece 4 and having a circular edge which engages with the internal circumferential surface of the liquid outlet end of the liquid storage cup 1. The annular pressing plate 5 tightly presses the filter piece 4 and the liquid percolation piece 3 and is locked by the at least two locking members 2. The annular pressing plate 5 can be made of stainless steel materials.

Figure 3:
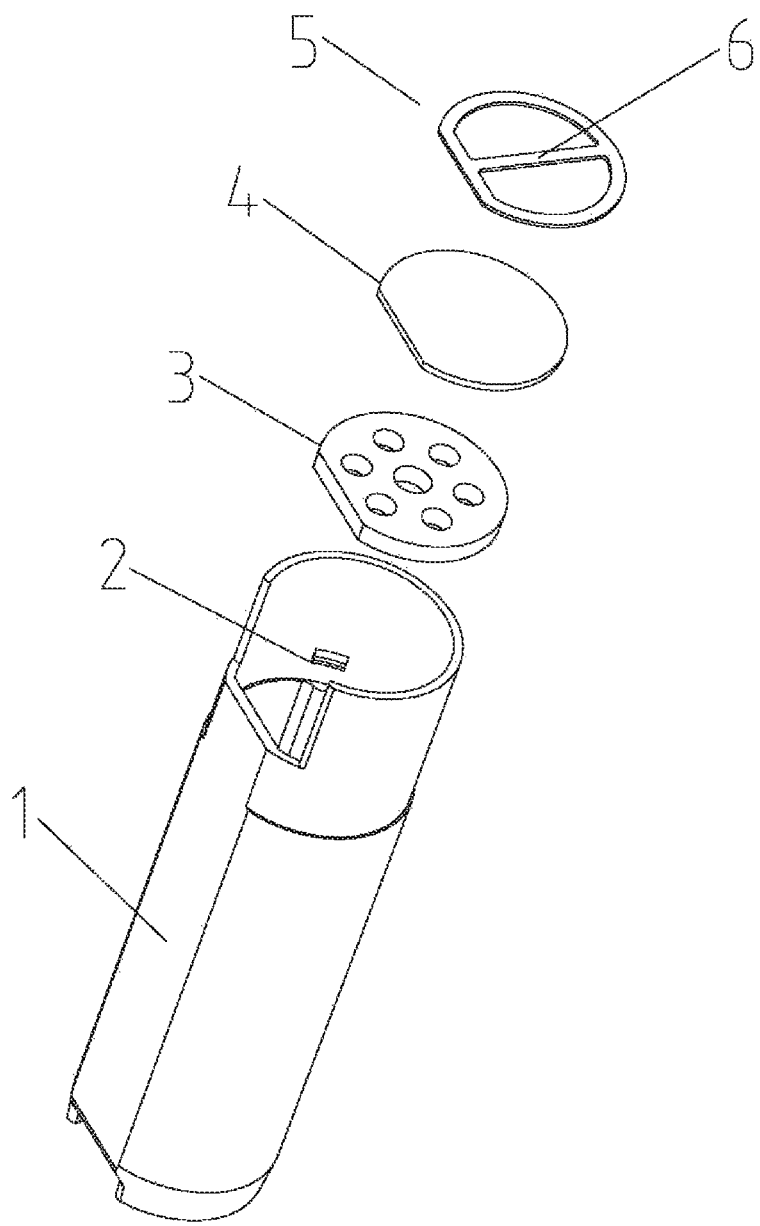
FIG. 3 is a perspective exploded view showing a second embodiment of an anti-leakage liquid storage device of an electronic cigarette of the present invention.
Figure 4:
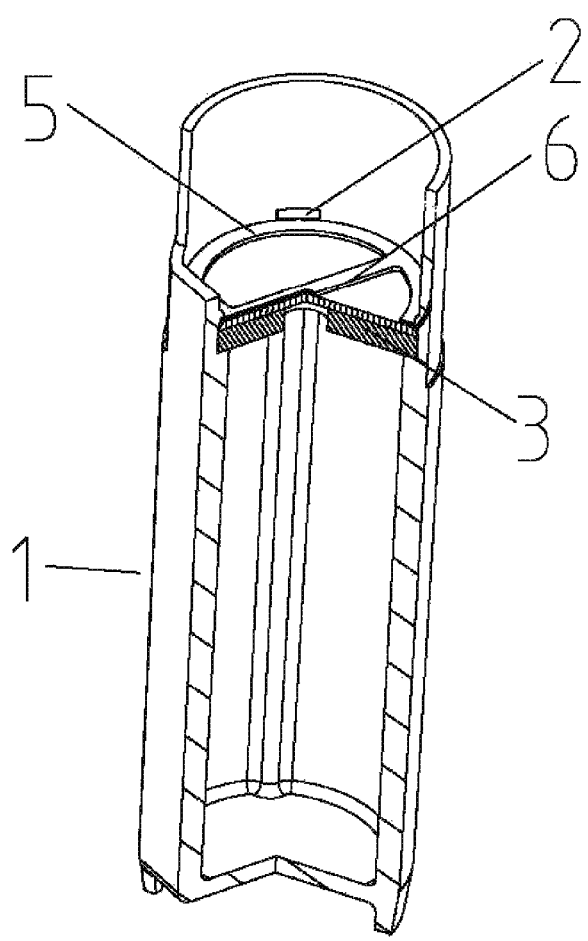
FIG. 4 is a schematic view of an assembled anti-leakage liquid storage device shown in FIG. 3, the anti-leakage liquid storage device being partially sectioned.

FIG. 3 and FIG. 4 show a second embodiment of an anti-leakage liquid storage device of an electronic cigarette of the present invention.

Referring to FIG. 3 and FIG. 4, the anti-leakage liquid storage device of the second embodiment differs from that of the first embodiment in that the annular pressing plate 5 is formed integrally with at least one reinforcing rib 6 at the middle thereof.

All the above are the preferred embodiments of the present invention, and the invention is intended to cover various modifications and equivalent arrangements included within the scope of the invention.

What is claimed is:

1. An anti-leakage liquid storage device of an electronic cigarette, comprising
    a cylindrical liquid storage cup,
    at least two locking members arranged at an inner wall of a liquid outlet end of the liquid storage cup,
    a liquid percolation piece having a plurality of liquid percolation holes and having a circular edge which engages with an internal circumferential surface of the liquid outlet end of the liquid storage cup,
    a filter piece with one side thereof abutting against the liquid percolation piece; and
    wherein the other side of the filter piece abuts against an annular pressing plate, the annular pressing plate has a circular edge which engages with the internal circumferential surface of the liquid outlet end of the liquid storage cup; the annular pressing plate is locked by the at least two locking members and tightly presses the filter piece and the liquid percolation piece;
    wherein the annular pressing plate is formed integrally with at least one reinforcing rib at the middle thereof.

* * * * *